US009056990B2

(12) United States Patent
Hayashi et al.

(10) Patent No.: US 9,056,990 B2
(45) Date of Patent: Jun. 16, 2015

(54) PHOSPHORUS-ATOM-CONTAINING OLIGOMER COMPOSITION, CURABLE RESIN COMPOSITION, CURED PRODUCT THEREOF, AND PRINTED CIRCUIT BOARD

(75) Inventors: Koji Hayashi, Ichihara (JP); Yutaka Satou, Ichihara (JP); Takamitsu Nakamura, Ichihara (JP)

(73) Assignee: DIC Corporation, Tokyo (JP)

( * ) Notice: Subject to any disclaimer, the term of this patent is extended or adjusted under 35 U.S.C. 154(b) by 0 days.

(21) Appl. No.: 13/821,449
(22) PCT Filed: Mar. 13, 2012
(86) PCT No.: PCT/JP2012/056409
§ 371 (c)(1),
(2), (4) Date: Mar. 7, 2013
(87) PCT Pub. No.: WO2012/124689
PCT Pub. Date: Sep. 20, 2012

(65) Prior Publication Data
US 2014/0008108 A1    Jan. 9, 2014

(30) Foreign Application Priority Data

Mar. 15, 2011   (JP) ................................ 2011-056205

(51) Int. Cl.
*C09D 5/18*     (2006.01)
*H05K 1/02*     (2006.01)
(Continued)

(52) U.S. Cl.
CPC ................ *C09D 5/18* (2013.01); *H05K 1/0326* (2013.01); *H05K 2201/012* (2013.01);
(Continued)

(58) Field of Classification Search
CPC .... C09D 5/18; C08G 59/4071; C08G 59/688; C08G 16/0281; C08G 16/0243
USPC ............. 525/507, 538; 523/451; 528/89, 108, 528/141, 158, 167
See application file for complete search history.

(56) References Cited

FOREIGN PATENT DOCUMENTS

| JP | 2001-354685 A | 12/2001 |
|----|----|----|
| JP | 2001354685 A * | 12/2001 |

(Continued)

OTHER PUBLICATIONS

International Search Report dated May 29, 2012, issued for PCT/JP2012/056409.

Primary Examiner — Randy Gulakowski
Assistant Examiner — Ha Nguyen
(74) Attorney, Agent, or Firm — Locke Lord LLP; James E. Armstrong, IV; Nicholas J. DiCeglie, Jr.

(57) ABSTRACT

A phosphorus-atom-containing oligomer is used as a curing agent for epoxy resin, the phosphorus-atom-containing oligomer being a mixture of a phosphorus-atom-containing compound represented by structural formula (1) below with n representing 0 and a phosphorus-atom-containing oligomer represented by structural formula (1) below with n representing 1 or more:

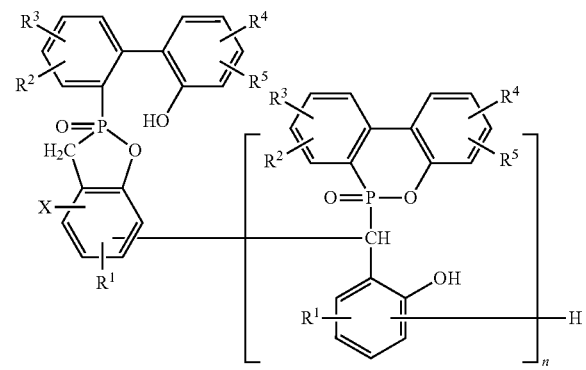

(where $R^1$ to $R^5$ each independently represent a hydrogen atom, an alkyl group having 1 to 4 carbon atoms, or the like; X represents a hydrogen atom or a structural unit represented by structural formula (x1) below:

[Chem. 2]

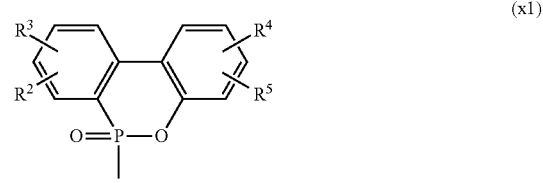

where, in structural formula (x1), $R^2$ to $R^5$ each independently represent a hydrogen atom, an alkyl group having 1 to 4 carbon atoms, or the like), wherein a content of the phosphorus-atom-containing oligomer represented by general structural formula (1) with n representing 1 or more is in the range of 5 to 90% on a peak area bases in GPC measurement.

6 Claims, 2 Drawing Sheets

(51) Int. Cl.
- C08G 59/00 (2006.01)
- C08G 59/40 (2006.01)
- C08G 59/62 (2006.01)
- C08G 63/02 (2006.01)
- C08L 63/00 (2006.01)
- C07F 9/6571 (2006.01)
- H05K 1/03 (2006.01)
- H05K 3/46 (2006.01)
- C08G 59/32 (2006.01)
- C08L 63/04 (2006.01)

(52) U.S. Cl.
CPC ..... *C07F 9/65717 2* (2013.01); *C08G 59/3272* (2013.01); *C08L 63/04* (2013.01); *H05K 1/02* (2013.01); *H05K 3/4676* (2013.01)

(56) References Cited

FOREIGN PATENT DOCUMENTS

| | | |
|---|---|---|
| JP | 2004-143166 A | 5/2004 |
| JP | 4953039 B2 | 8/2011 |
| WO | WO-2011/102211 A1 | 8/2011 |

* cited by examiner

PHOSPHORUS-ATOM-CONTAINING OLIGOMER COMPOSITION, CURABLE RESIN COMPOSITION, CURED PRODUCT THEREOF, AND PRINTED CIRCUIT BOARD

TECHNICAL FIELD

The present invention relates to a phosphorus-atom-containing oligomer composition that has excellent solvent solubility and exhibits excellent flame retardancy and heat resistance when formed into a cured product, a curable resin composition that uses the oligomer composition as a curing agent for epoxy resin, a cured product thereof, and a printed circuit board formed by using the curable resin composition.

BACKGROUND ART

Epoxy resin compositions that contain epoxy resin and curing agents for epoxy resin as essential components have excellent physical properties such as high heat resistance and moisture resistance and are thus widely used in electronic parts such as semiconductor encapsulating materials and printed circuit boards, conductive adhesives such as conductive paste, other adhesives, matrices for composite materials, paints, photoresist materials, and developer materials.

In recent years, these various usages and advanced material usages in particular require further improvements in performance such as heat resistance, moisture resistance, and solder resistance. In particular, on-vehicle electronic devices required to achieve particularly high reliability are now being installed more in engine rooms where the temperature is high than in cabins and the reflow temperature is increasing due to use of lead-free solder. Thus, a highly heat resistant material that has a higher glass transition point and is capable of withstanding a heat peeling resistance test (hereinafter referred to as "T288 test") is desired.

When epoxy resin compositions are used as printed circuit board materials, halogen-based flame retardants such as bromine are blended together with antimony compounds in order to impart flame retardancy. However, due to recent environmental and safety concerns, an environmentally friendly and safety-oriented approach of achieving flame retardancy without using halogen-based flame retardants that would generate dioxin and antimony compounds that are possibly carcinogenic has been strongly demanded. In the field of printed circuit board materials, use of halogen-based flame retardants has become a factor that harms high temperature exposure reliability. Thus there is high expectation for halogen-free materials.

To satisfy the required properties, an epoxy resin composition having flame retardancy and heat resistance has been disclosed in PTL 1. According to this technology, a reaction product obtained by reacting 9,10-dihydro-9-oxa-10-phosphaphenanthrene-10-oxide (hereinafter simply referred to as "HCA") and p-hydroxybenzaldehyde is reacted with phenol to obtain a phosphorus-atom-containing bisphenol and this phosphorus-atom-containing bisphenol is used as an epoxy resin raw material or an epoxy resin curing agent.

However, phosphorus-atom-containing bisphenols have very high crystallinity and little or no solvent solubility and thus they cannot be prepared into varnish for printed circuit board materials. Moreover, the flame retardancy of cured products made by using phosphorus-atom-containing bisphenols as an epoxy resin curing agent has been insufficient. Since the melting point of the phosphorus-atom-containing bisphenols is 200° C. or higher, they are extremely difficult to produce industrially.

NPL 1 below discloses a technology of obtaining an intermediate product by reacting HCA with p-hydroxybenzaldehyde and oligomerizing the intermediate product in THF.

However, according to the technology disclosed in NPL 1, the crystallinity of the reaction product from the intermediate HCA and p-hydroxybenzaldehyde is very high and the solvent solubility is poor. Thus, as described in NPL 1, THF which has a low flash point and is thus highly unsafe needs to be used in the subsequent reactions, which makes industrial production impossible. Moreover, the solvent solubility of the resulting oligomer itself is low and the oligomer is difficult to be prepared into varnish for printed circuit board materials.

PTL 2 below discloses a technology of producing a phosphorus-atom-containing phenol compound by reacting HCA with hydroxybenzaldehyde. However, the phenol compound described in PTL 2 is a monofunctional phenol compound and has very high crystallinity and low solvent solubility. When this compound is used as a curing agent for epoxy resin, sufficient flame retardancy is not obtained.

CITATION LIST

Patent Literature

PTL 1: Japanese Unexamined Patent Application 2004-143166

PTL 2: Japanese Unexamined Patent Application Publication No. 2001-354685

Non Patent Literature

NPL 1: Ying Ling Liu, "Flame-retardant epoxy resins from novel phosphorus-containing novolac", Polymer, vol. 42 (2001) pp. 3445-3454

SUMMARY OF INVENTION

Technical Problem

Accordingly, an object of the present invention is to provide a phosphorus-atom-containing oligomer that has excellent flame retardancy and heat resistance when cured into a cured product and has dramatically improved solubility in organic solvents, a curable resin composition containing this oligomer and a cured product thereof, and a printed circuit board made by using the composition.

Solution to Problem

The inventors of the subject invention have conducted extensive studies to achieve the object described above and found that a phosphorus-atom-containing oligomer composition that has a particular molecular structure obtained by reacting and oligomerizing a phosphorus-atom-containing compound such as HCA and a o-hydroxybenzaldehyde compound exhibits excellent solubility in organic solvents and gives a cured product that exhibits excellent flame retardancy, has a high glass transition point, and can withstand the T288 test when the oligomer composition is used as a curing agent for epoxy resin, a raw material for epoxy resin, an additive for thermosetting resin, or the like and cured. Thus the present invention has been made.

In other words, the present invention relates to a phosphorus-atom-containing oligomer composition including a mixture of a phosphorus-atom-containing compound represented by structural formula (1) below with n representing 0 and a phosphorus-atom-containing oligomer represented by structural formula (1) below with n representing 1 or more:

[Chem. 1]

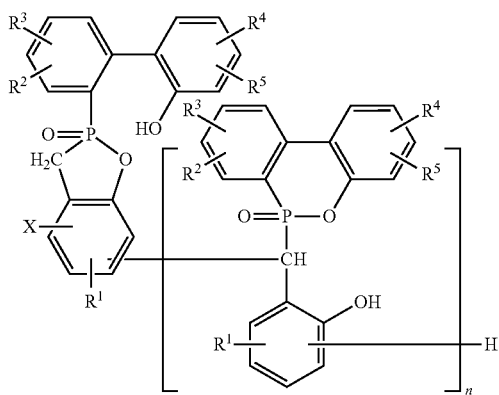

(1)

(where $R^1$ to $R^5$ each independently represent a hydrogen atom, an alkyl group having 1 to 4 carbon atoms, an alkoxy group having 1 to 4 carbon atoms, or a phenyl group; X represents a hydrogen atom or a structural unit represented by structural formula (x1) below:

[Chem. 2]

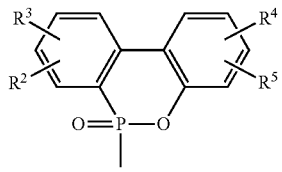

(x1)

where, in structural formula (x1), $R^2$ to $R^5$ each independently represent a hydrogen atom, an alkyl group having 1 to 4 carbon atoms, an alkoxy group having 1 to 4 carbon atoms, or a phenyl group; and n represents the number of repeating units and is an integer of 0 or more), wherein a content of the phosphorus-atom-containing oligomer represented by general structural formula (1) with n representing 1 or more is in the range of 5 to 90% on a peak area basis in GPC measurement.

The present invention further relates to a curable resin composition including an epoxy resin and a curing agent as essential components, wherein the phosphorus-atom-containing oligomer composition described above is used as the curing agent.

The present invention also relates to a cured product obtained by curing the curable resin composition described above.

The present invention also relates to a printed circuit board obtained by blending an organic solvent with the curable resin composition described above to prepare a varnish-type resin composition, impregnating a reinforcing substrate with the varnish-type resin composition, placing a copper foil thereon, and conducting thermal press bonding.

Advantageous Effects of Invention

The present invention provides a phosphorus-atom-containing oligomer composition that has dramatically improved solubility in organic solvents and exhibits excellent flame retardancy and heat resistance when cured into a cured product, a curable resin composition containing the oligomer composition and a cured product thereof, and a printed circuit board manufactured by using the composition.

DESCRIPTION OF EMBODIMENTS

Figure 1:
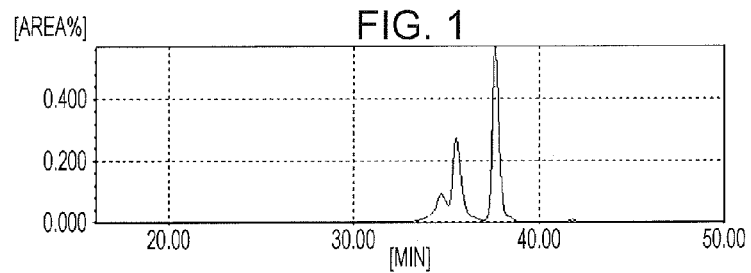
FIG. 1 is a GPC chart of a phosphorus-atom-containing oligomer composition (A-1) obtained in Example 1.

The present invention will now be described in detail.
A phosphorus-atom-containing oligomer composition of the present invention is a mixture of a phosphorus-atom-containing compound represented by structural formula (1) below with n representing 0 and a phosphorus-atom-containing oligomer represented by structural formula (1) below with n representing 1 or more:

[Chem. 3]

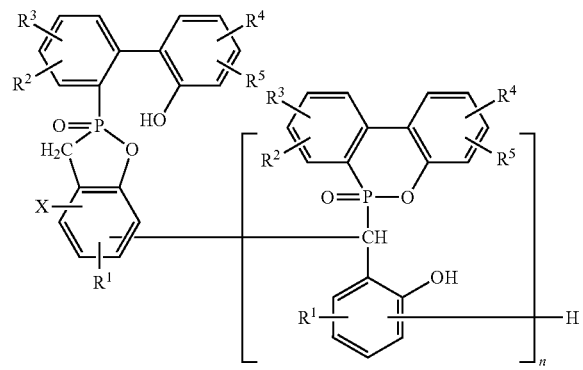

(1)

(In the formula, $R^1$ to $R^5$ each independently represent a hydrogen atom, an alkyl group having 1 to 4 carbon atoms, an alkoxy group having 1 to 4 carbon atoms, or a phenyl group; X represents a hydrogen atom or a structural unit represented by structural formula (x1) below:

[Chem. 4]

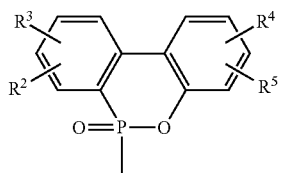

where in formula (x1), $R^2$, $R^3$, $R^4$, and $R^5$ each independently represent a hydrogen atom, an alkyl group having 1 to 4 carbon atoms, an alkoxy group having 1 to 4 carbon atoms, a phenyl group, or an aralkyl group) and n represents the number of repeating units and is an integer of 0 or more). Because the phosphorus-atom-containing compound and the phosphorus-atom-containing oligomer have a basic structure represented by structural formula (1) above, excellent flame retardancy is exhibited when the composition is cured, the glass transition point is high, and the heat peeling resistance is high.

Among chemical structures represented by structural formula (1) above, those with X representing a hydrogen atom are the following compounds represented by structural formulae (1-1) to (1-4) below.

[Chem. 5]

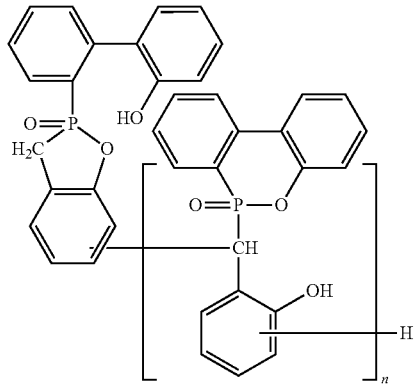
(1-1)

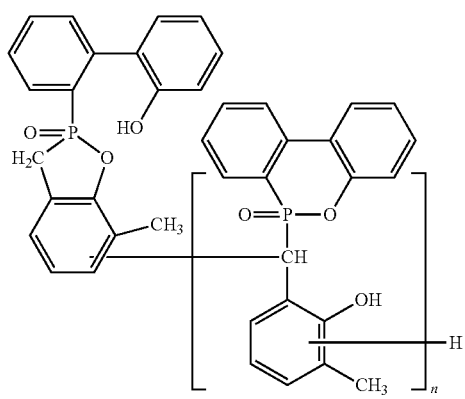
(1-2)

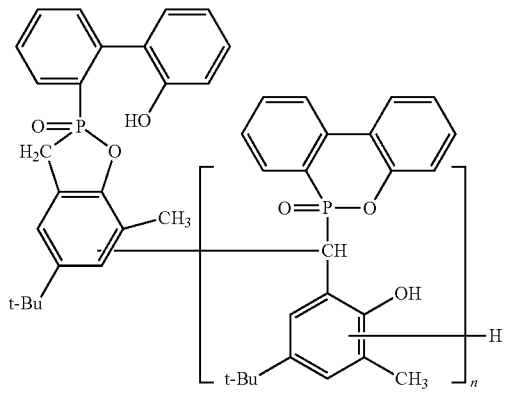
(1-3)

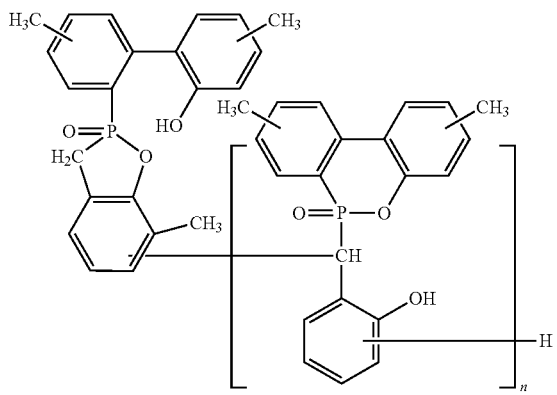
(1-4)

Among chemical structures represented by structural formula (1) above, those with X representing a structure represented by structural formula (x1) above are as follows:

[Chem. 6]

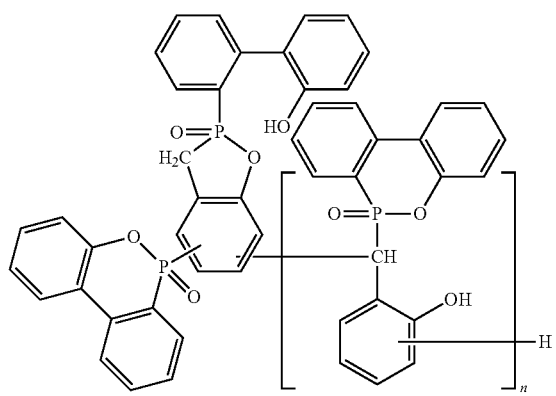
(1-5)

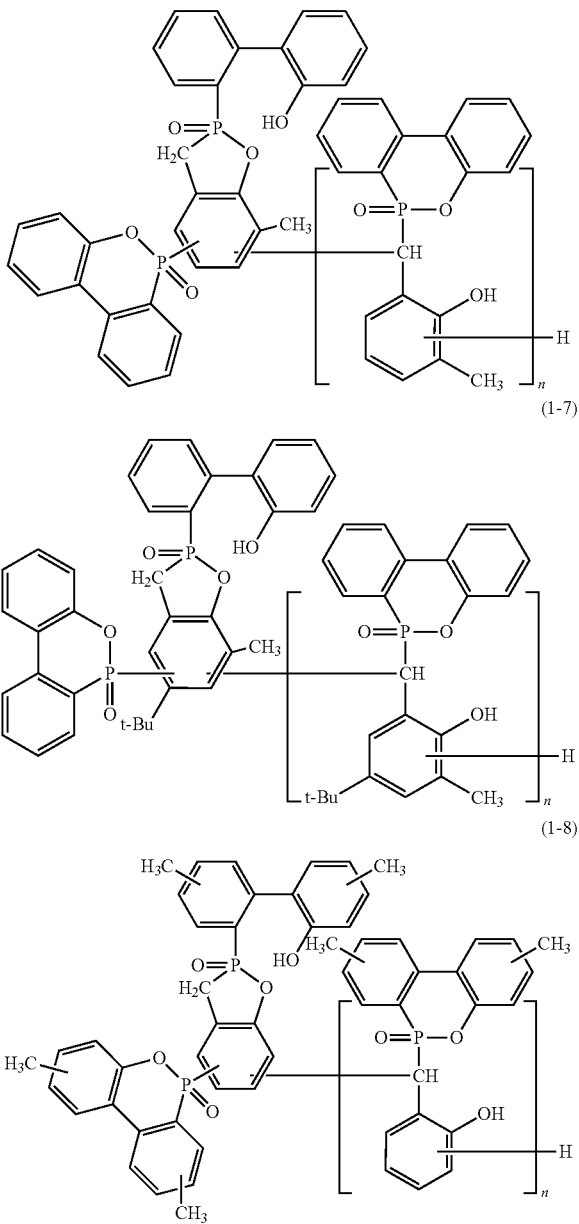

(1-6)

(1-7)

(1-8)

In the present invention, X in structural formula (1) is either a hydrogen atom or a unit represented by structural formula (x1) above. From the viewpoint of flame retardancy, X is preferably the unit represented by structural formula (x1). Thus, a mixture of a phosphorus-atom-containing compound (n=0) and a phosphorus-atom-containing oligomer (component with n representing 1 or more) each represented by any one of structural formulae (1-5) to (1-8) above is preferred.

$R^1$ to $R^5$ in structural formula (1) and $R^2$ to $R^5$ in structural formula (x1) each independently represent a hydrogen atom, an alkyl group having 1 to 4 carbon atoms, an alkoxy group having 1 to 4 carbon atoms, or a phenyl group. Examples of the alkyl group having 1 to 4 carbon atoms include a methyl group, an ethyl group, a n-propyl group, an i-propyl group, and a tert-butyl group. Examples of the alkoxy group having 1 to 4 carton atoms include a methoxy group, an ethoxy group, a n-propyloxy group, an i-propyloxy group, and a tert-butoxy group.

In the present invention, $R^1$ to $R^5$ in structural formula (1) and $R^2$ to $R^5$ in structural formula (x1) preferably each independently represent a hydrogen atom or an alkyl group having 1 to 4 carbon atoms. Preferably, all of $R^1$ to $R^5$ in structural formula (1) and $R^2$ to $R^5$ in structural formula (x1) represent a hydrogen atom from the viewpoint of flame retardancy.

The phosphorus-atom-containing oligomer composition is a mixture of a phosphorus-atom-containing compound represented by structural formula (1) with n representing 0 (hereinafter this component is simply referred to as "component with n representing 0") and a phosphorus-atom-containing oligomer represented by structural formula (1) with n representing 1 or more, as described above. The phosphorus-atom-containing oligomer content in the mixture is in the range of 5 to 90% on a peak area basis in GPC measurement. Because the content is within this range, the solubility of the oligomer in organic solvents is high and flame retardancy of the cured product obtained therefrom is dramatically improved.

The phosphorus-atom-containing oligomer composition preferably contains 40 to 85% of the phosphorus-atom-containing oligomer represented by structural formula (1) with n representing 1 or more on a peak area basis in GPC measurement since the solubility in organic solvents is high and the cured product made therefrom exhibits excellent flame retardancy.

Here, the phosphorus-atom-containing oligomer content, i.e., the content of the component represented by structural formula (1) above with n representing 1 or more, refers to the ratio of the peak area that is less than 36.0 minutes in a GPC chart taken under the following conditions:

<GPC Measurement Conditions>

4) GPC: Measurement conditions are as follows:
Measurement instrument: "HLC-8220 GPC" produced by Tosoh Corporation
Column: Guardcolumn "HXL-L" produced by Tosoh Corporation
"TSK-GEL G2000HXL" produced by Tosoh Corporation
"TSK-GEL G2000HXL" produced by Tosoh Corporation
"TSK-GEL G3000HXL" produced by Tosoh Corporation
"TSK-GEL G4000HXL" produced by Tosoh Corporation
Detector: RI (differential refractometer)
Data processing: "GPC-8020 Model II, version 4.10" produced by Tosoh Corporation
Measurement conditions
Column temperature: 40° C.
Developing solvent: tetrahydrofuran
Flow rate: 1.0 ml/min
Standard: In accordance with a measurement manual of "GPC-8020 Model II, version 4.10" described above, monodisperse polystyrenes below whose molecular weights are known were used:
(Polystyrenes Used)
"A-500" produced by Tosoh Corporation
"A-1000" produced by Tosoh Corporation
"A-2500" produced by Tosoh Corporation
"A-5000" produced by Tosoh Corporation
"F-1" produced by Tosoh Corporation
"F-2" produced by Tosoh Corporation
"F-4" produced by Tosoh Corporation
"F-10" produced by Tosoh Corporation
"F-20" produced by Tosoh Corporation
"F-40" produced by Tosoh Corporation
"F-80" produced by Tosoh Corporation
"F-128" produced by Tosoh Corporation
Sample: Sample prepared by filtering a tetrahydrofuran solution having a resin solid content of 1.0 mass % with a microfilter (50 µl).

In the present invention, when the phosphorus-atom-containing oligomer content, i.e., the content of the component with n representing 1 or more, is 5% or more on a peak area basis in GPC measurement, excellent solvent solubility is exhibited. When the content is 90% or less, the fluidity in melting and fluidity and impregnability of varnish prepared therefrom become excellent. Here, the rest is the component with n representing 0. Accordingly, the content of the component with n representing 0 (phosphorus-atom-containing compound) in the phosphorus-atom-containing oligomer composition of the present invention is 95 to 10% on a peak area basis in GPC measurement. In the present invention, in order to maintain solvent solubility and fluidity and achieve high heat resistance as a cured product, a high glass transition point, and excellent performance in T288 test, the phosphorus-atom-containing oligomer (component with n representing 1 or more) content in the composition is preferably within the range of 40 to 75% and the phosphorus-atom-containing compound (component with n representing 0) content is preferably within the range of 60 to 25%.

To be more specific, the content of the component with n representing 0 (phosphorus-atom-containing compound) is preferably 95 to 10%, the content of the phosphorus-atom-containing oligomer with n representing 1 (hereinafter simply referred to as "component with n representing 1") is preferably 3 to 50%, and the content of a phosphorus-atom-containing oligomer with n representing 2 or more (hereinafter simply referred to as "component with n representing 2 or more") is preferably 2 to 45% from the viewpoint of solvent solubility. In particular, the content of the component with n representing 0 is preferably 60 to 25%, the content of the component with n representing 1 is preferably 10 to 45%, and the content of the component with n representing 2 or more is preferably 10 to 40% since the solvent solubility, fluidity, and heat resistance become well balanced.

The phosphorus atom content in the phosphorus-atom-containing oligomer composition is preferably within the range of 9 to 12 mass % from the viewpoint of flame retardancy. The phosphorus content is a value measured in accordance with "JIS standard K0102 46".

The phosphorus-atom-containing oligomer composition described in detail above is preferably prepared by the production method described below since the composition exhibits high solubility in organic solvents and a cured product obtained therefrom exhibits excellent heat resistance.

That is, a compound (a1) represented by structural formula (a1) below

[Chem. 7]

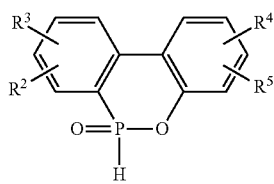

(a1)

(where $R^2$ to $R^5$ each independently represent a hydrogen atom, an alkyl group having 1 to 4 carbon atoms, an alkoxy group having 1 to 4 carbon atoms, or a phenyl group) and a compound (a2) represented by structural formula (a2) below:

[Chem. 8]

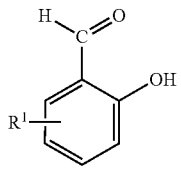

(a2)

(where $R^1$ represents a hydrogen atom, an alkyl group having 1 to 4 carbon atoms, an alkoxy group having 1 to 4 carbon atoms, or a phenyl group) are blended so that the molar ratio [compound (a1)/compound (a2)] is 0.01/1.0 to 0.99/1.0, a reaction is carried out at 100 to 200° C. in the presence or absence of an acid catalyst, the compound (a1) is added thereto in a total amount of 1.01 to 3.0 times the feed amount of the compound (a2) on a molar basis, and a reaction is carried out at 140 to 220° C. As a result, the desired phosphorus-atom-containing oligomer composition can be obtained.

In the present invention, when a phosphorus-atom-containing oligomer composition is produced by this method, precipitation of reaction intermediates can be satisfactorily suppressed and the molecular weight can be easily increased.

Examples of the alkyl group having 1 to 4 carbon atoms for $R^2$, $R^3$, $R^4$, and $R^5$ in structural formula (a1) above include a methyl group, an ethyl group, a n-propyl group, an i-propyl group, and a tert-butyl group. Examples of the alkoxy group having 1 to 4 carbon atoms include a methoxy group, an ethoxy group, a n-propyloxy group, an i-propyloxy group, and a tert-butoxy group. In the present invention, all of the $R^2$, $R^3$, $R^4$, and $R^5$ in the compound (a1) are hydrogen atoms from the viewpoint of flame retardancy. $R^1$ in structural formula (a2) in the compound (a2) is an alkyl group having 1 to 4 carbon atoms, an alkoxy group having 1 to 4 carbon atoms, or a phenyl group. Examples of the alkyl group having 1 to 4 carbon atoms include a methyl group, an ethyl group, a n-propyl group, an i-propyl group, and a tert-butyl group. Examples of the alkoxy group having 1 to 4 carbon atoms include a methoxy group, an ethoxy group, a n-propyloxy group, an i-propyloxy group, and a tert-butoxy group. $R^1$ is preferably a hydrogen atom among these since the reactivity with the compound (a1) is high and the cured product obtained therefrom exhibits excellent flame retardancy.

As mentioned above, this method may be conducted without any catalyst and the reaction is preferably conducted in the absence of a catalyst since the selectivity and yield of the compound ultimately obtained are high. If a catalyst is to be used, examples of the catalyst that can be used include inorganic acids such as hydrochloric acid, sulfuric acid, and phosphoric acid, organic acids such as methane sulfonic acid, p-toluene sulfonic acid, and oxalic acid, and Lewis acids such as boron trifluoride, aluminum chloride anhydride, and zinc chloride. The amount used is, for example, in the range of 0.1 to 5.0 mass % relative to the total weight of the feed materials from the viewpoint of preventing degradation of electrical insulation of the cured product.

Since the compound (a2) is liquid, the reaction can be conducted by using this compound as the organic solvent. However, from the viewpoint of improving workability etc., other organic solvents may be used. Examples of the organic solvents used include non-ketone-based organic solvents such as alcohol-based organic solvents and hydrocarbon-based organic solvents. Examples of the alcohol-based organic solvents include propylene glycol monomethyl ether and the like and examples of the hydrocarbon-based organic solvents include toluene and xylene.

After completion of the reaction, the product is dried at a reduced pressure to obtain a desired substance.

A curable resin composition of the present invention contains an epoxy resin and a curing agent as essential components and the phosphorus-atom-containing oligomer composition described above is used as the curing agent.

Various epoxy resins can be used as the epoxy resin. Examples thereof include bisphenol-type epoxy resins such as bisphenol A-type epoxy resin and bisphenol F-type epoxy resin; biphenyl-type epoxy resins such as biphenyl-type epoxy resin and tetramethyl biphenyl-type epoxy resin; a novolac-type epoxy resins such as phenol novolac-type epoxy resin, cresol novolac-type epoxy resin, bisphenol A novolac-type epoxy resin, an epoxy compound of a condensate between a phenol and an aromatic aldehyde having a phenolic hydroxyl group, and biphenyl novolac-type epoxy resin; triphenyl methane-type epoxy resin; tetraphenylethane-type epoxy resin; dicyclopentadiene-phenol-addition reaction-type epoxy resin; phenol aralkyl-type epoxy resin; epoxy resin having a naphthalene skeleton in the molecular structure, such as naphthol novolac-type epoxy resin, naphthol aralkyl-type epoxy resin, naphthol-phenol-co-condensed novolac-type epoxy resin, naphthol-cresol co-condensed novolac-type epoxy resin, diglycidyloxy naphthalene, and 1,1-bis(2,7-diglycidyloxy-1-naphthyl)alkane; and phosphorus-atom-containing epoxy resin. These epoxy resins may be used alone or in combination.

Examples of the phosphorus-atom-containing epoxy resin include an epoxidized phenolic resin obtained by reaction of 9,10-dihydro-9-oxa-10-phosphaphenanthrene-10-oxide (hereinafter simply referred to as "HCA") and a quinone compound, an epoxy resin prepared by modifying a phenol novolac-type epoxy resin with HCA, an epoxy resin prepared by modifying a cresol novolac-type epoxy resin with HCA, an epoxy resin prepared by modifying a bisphenol A-type epoxy resin with a phenolic resin obtained by reacting HCA and a quinone compound, and an epoxy resin obtained by modifying a bisphenol F-type epoxy resin with a phenolic resin obtained by reacting HCA and a quinone compound.

Of the epoxy resins described above, an epoxy resin that contains a novolac-type epoxy resin and a naphthalene skeleton in the molecular structure is preferred from the viewpoint of heat resistance. From the viewpoint of solvent solubility, a bisphenol-type epoxy resin and a novolac-type epoxy resin are preferred.

The blend ratios of the epoxy resin and the phosphorus-atom-containing oligomer in the curable resin composition of the present invention are not particularly limited. From the viewpoint of properties of the cured product, the blend ratios are such that 0.7 to 1.5 equivalents of active hydrogen in the phosphorus-atom-containing oligomer is contained per equivalent of the total of epoxy groups in the epoxy resin.

The curable resin composition of the present invention may additionally use a curing agent other than the phosphorus-atom-containing oligomer composition described above as the epoxy resin curing agent as long as the effects of the present invention are not impaired. Examples of such other curing agent include amine-based compounds, amide-based compounds, acid anhydride-based compounds, and phenol-based compounds. Examples of the amine-based compounds include diaminodiphenylmethane, diethylenetriamine, triethylenetetramine, diaminodiphenylsulfone, isophoronediamine, imidazole, $BF_3$-amine complexes, and guanidine derivatives. Examples of the amide-based compound include dicyandiamide and polyamide resins synthesized from dimers of linoleic acid and ethylenediamine. Examples of the acid anhydride-based compounds include phthalic anhydride, trimellitic anhydride, pyromellitic anhydride, maleic anhydride, tetrahydrophthalic anhydride, methyltetrahydrophthalic anhydride, methylnadic anhydride, hexahydrophthalic anhydride, and methylhexahydrophthalic anhydride. Examples of the phenol-based compounds include polyvalent phenol compounds such as phenol novolac resin, cresol novolac resin, aromatic hydrocarbon formaldehyde resin-modified phenolic resin, dicyclopentadiene phenol addition-type resin, phenol aralkyl resin (xyloc resin), naphthol aralkyl resin, trisphenylol methane resin, tetraphenylol ethane resin, naphthol novolac resin, naphthol phenol co-condensed novolac resin, naphthol cresol co-condensed novolac resin, biphenyl-modified phenolic resin (polyvalent phenol compound in which phenol nuclei are linked through bismethylene groups), biphenyl-modified naphthol resin (polyvalent naphthol compound in which phenol nuclei are linked through bismethylene groups) aminotriazine-modified phenolic resin (compound having a phenol skeleton, a triazine ring, and a primary amino group in the molecular structure), and an alkoxy-group-containing aromatic ring-modified novolac resin (polyvalent phenol compound in which phenol nuclei and alkoxy-group-containing aromatic rings are liked through formaldehyde).

Of these, compounds having a large number of aromatic skeletons in the molecular structure are preferred since the cured product will have low heat expandability. In particular, phenol novolac resin, cresol novolac resin, aromatic hydrocarbon formaldehyde resin-modified phenolic resin, phenol aralkyl resin, naphthol aralkyl resin, naphthol novolac resin, naphthol-phenol co-condensed novolac resin, naphthol-cresol co-condensed novolac resin, biphenyl-modified phenolic resin, biphenyl modified naphthol resin, aminotriazine-modified phenolic resin, and alkoxy-group-containing aromatic ring-modified novolac resin (polyvalent phenolic compound in which phenol nuclei and alkoxy-group-containing aromatic rings are linked through formaldehyde) are preferred from the viewpoint of low heat expandability.

The above-described aminotriazine-modified phenolic resin, i.e., a compound having a phenol skeleton, a triazine ring, and a primary amino group in the molecular structure, preferably has a molecular structure obtained by a condensation reaction of a triazine compound, phenol, and aldehyde since the cured product will exhibit high flame retardancy.

Other curing agents mentioned above are preferably used so that the phosphorus atom content in the solid matter in the curable resin composition of the present invention is within the range of 1 to 9% from the viewpoint of the flame retardancy of the cured product.

If needed, a curing accelerator may be used together with the curable resin composition of the present invention. Various types of compounds can be used as the curing accelerator. Examples thereof include phosphorus-based compounds, tertiary amines, imidazoles, organic acid metal salts, Lewis acids, and amine complex salts. When the composition is used in semiconductor encapsulating materials, triphenylphosphine is preferred among the phosphorus-based compounds and 2-ethyl-4-methylimidazole is preferred among the amine-based compounds since they offer excellent curability, heat resistance, electrical properties, moisture resistance reliability, etc. The amount of the curing accelerator used here is preferably in the range of 0.01 to 1 mass % of the curable resin composition.

The curable resin composition of the present invention described in detail above is characterized in having excellent solvent solubility as discussed above. Accordingly, the curable resin composition preferably contains an organic solvent in addition to the components described above. Examples of the organic solvent that can be used here include methyl ethyl ketone, acetone, dimethylformamide, methyl isobutyl ketone, methoxy propanol, cyclohexanone, methyl cellosolve, ethyl diglycol acetate, and polypropylene glycol monomethyl ether acetate. The choice and the appropriate amount of use may be adequately selected depending on the usage. For example, for printed circuit board usage, the organic solvent is preferably an alcohol-based organic solvent having a boiling point of 160° C. or less, such as methyl ethyl ketone, acetone, or 1-methoxy-2-propanol or an organic solvent that contains a carbonyl group, and the amount thereof is preferably 40 to 80 mass % on a nonvolatile matter basis. For usage of adhesive films for forming build-up structures, the organic solvent is preferably a ketone such as acetone, methyl ethyl ketone, or cyclohexanone, an acetate such as ethyl acetate, butyl acetate, cellosolve acetate, propylene glycol monomethyl ether acetate, or carbitol acetate, a carbitol such as cellosolve or butyl carbitol, an aromatic hydrocarbon such as toluene or xylene, dimethylformamide, dimethylacetamide, or N-methylpyrrolidone, and the amount thereof is preferably 30 to 60 mass % on a nonvolatile matter basis.

The curable resin composition described above may contain a non-halogen flame retardant to impart flame retardancy for printed circuit board usage, within the range that does not degrade the reliability.

Examples of the non-halogen flame retardant include phosphorus-based flame retardants, nitrogen-based flame retardants, silicone-based flame retardants, inorganic flame retardants, and organic metal salt-based flame retardants. There is no limit on the use thereof. These flame retardants may be used alone or in combination with two or more flame retardants of the same system or different systems.

The phosphorus-based flame retardants may be organic or inorganic. Examples of the inorganic compound include ammonium phosphates such as red phosphorus, monoammonium phosphate, diammonium phosphate, triammonium phosphate, and ammonium polyphosphate, and inorganic nitrogen-containing phosphorus compound such as amide phosphate.

The red phosphorus is preferably surface-treated to prevent hydrolysis and the like. Examples of the surface-treating method include (i) a method with which red phosphorus is coated with an inorganic compound such as magnesium hydroxide, aluminum hydroxide, zinc hydroxide, titanium hydroxide, bismuth oxide, bismuth hydroxide, bismuth nitrate, or a mixture thereof, (ii) a method with which red phosphorus is coated with a mixture of an inorganic compound such as magnesium hydroxide, aluminum hydroxide, zinc hydroxide, or titanium hydroxide and a thermosetting resin such as a phenolic resin, and (iii) a method with which red phosphorus is coated with an inorganic compound such as magnesium hydroxide, aluminum hydroxide, zinc hydroxide, or titanium hydroxide and then with a thermosetting resin such as a phenolic resin on the coating of the inorganic compound.

Examples of the organic phosphorus-based compound include common organic phosphorus-based compounds such as phosphate compounds, phosphonate compounds, phosphine compounds, phosphine oxide compounds, phospholan compounds, and organic nitrogen-containing phosphorus compounds; and cyclic organic phosphorus compounds and derivatives thereof obtained by reaction with a compound such as an epoxy resin or a phenolic resin, such as 9,10-dihydro-9-oxa-10-phosphaphenanthrene-10-oxide, 10-(2,5-dihydroxyphenyl)-10H-9-oxa-10-phosphaphenanthrene-10-oxide, and 10-(2,7-dihydroxynaphthyl)-10H-9-oxa-10-phosphaphenanthrene-10-oxide.

The amount of the compound blended is appropriately selected on the basis of the type of the phosphorus-based flame retardant, other components of the curable resin composition, and the desired degree of flame retardancy. For example, when red phosphorus is used as a non-halogen flame retardant, 0.1 to 2.0 parts by mass of red phosphorus is preferably used in 100 parts by mass of a curable resin composition containing an epoxy resin, a curing agent, the non-halogen flame retardant, and other fillers and additives. When an organic phosphorus compound is used, preferably 0.1 to 10.0 parts by mass and more preferably 0.5 to 6.0 parts by mass of the organic phosphorus compound is blended.

The phosphorus-based flame retardant may be used together with hydrotalcite, magnesium hydroxide, boride compounds, zirconium oxide, black dye, calcium carbonate, zeolite, zinc molybdate, activated carbon, or the like.

Examples of the nitrogen-based flame retardant include triazine compounds, cyanuric acid compounds, isocyanuric acid compounds, and phenothiazine. Triazine compounds, cyanuric acid compounds, and isocyanuric acid compounds are preferred.

Examples of the triazine compounds include melamine, acetoguanamine, benzoguanamine, melon, melam, succinoguanamine, ethylenedimelamine, melamine polyphosphate, and triguanamine, aminotriazine sulfate compounds such as guanylmelamine sulfate, melem sulfate, and melam sulfate, phenolic resins modified with the aminotriazines, and aminotriazine-modified phenolic resins further modified with tung oil, isomerized linseed oil, or the like.

Examples of the cyanuric acid compounds include cyanuric acid and melamine cyanurate.

The amount of the nitrogen-based flame retardant blended is appropriately selected on the basis of the type of the nitrogen-based flame retardant, other components of the curable resin composition, and the desired degree of flame retardancy. For example, preferably 0.05 to 10 parts by mass and particularly preferably 0.1 to 5 parts by mass of the nitrogen-based flame retardant is contained in 100 parts by mass of a curable resin composition containing an epoxy resin, a curing agent, the non-halogen flame retardant, and other fillers and additives.

The nitrogen-based flame retardant may be used together with a metal hydroxide, a molybdenum compound, or the like.

The silicone-based flame retardant may be any organic compound containing a silicon atom. Examples thereof include silicone oil, silicone rubber, and silicone resin.

The amount of the silicone-based flame retardant blended is appropriately selected on the basis of the type of the silicone-based flame retardant, other components of the curable resin composition, and the desired degree of flame retardancy. For example, preferably 0.05 to 20 parts by mass of the silicone-based flame retardant is contained in 100 parts by mass of a curable resin composition containing an epoxy resin, a curing agent, the non-halogen flame retardant, and other fillers and additives. The silicone-based flame retardant may be used together with a molybdenum compound, alumina, or the like.

Examples of the inorganic flame retardant include metal hydroxides, metal oxides, metal carbonate compounds, metal powder, boron compounds, and low-melting-point glass.

Examples of the metal hydroxide include aluminum hydroxide, magnesium hydroxide, dolomite, hydrotalcite, calcium hydroxide, barium hydroxide, and zirconium hydroxide.

Examples of the metal oxides include zinc molybdate, molybdenum trioxide, zinc stannate, tin oxide, aluminum oxide, iron oxide, titanium oxide, manganese oxide, zirconium oxide, zinc oxide, molybdenum oxide, cobalt oxide, bismuth oxide, chromium oxide, nickel oxide, copper oxide, and tungsten oxide.

Examples of the metal carbonate compounds include zinc carbonate, magnesium carbonate, calcium carbonate, barium carbonate, basic magnesium carbonate, aluminum carbonate, iron carbonate, cobalt carbonate, and titanium carbonate.

Examples of the metal powder include aluminum, iron, titanium, manganese, zinc, molybdenum, cobalt, bismuth, chromium, nickel, copper, tungsten, and tin powders.

Examples of the boron compounds include zinc borate, zinc metaborate, barium metaborate, boric acid, and borax.

Examples of the low-melting-point glass include Seaplea (Bokusui Brown Co Ltd.), hydrated glass $SiO_2$—MgO—$H_2O$, and glassy compounds based on PbO—$B_2O_3$, ZnO—$P_2O_5$—MgO, $P_2O_5$—$B_2O_3$—PbO—MgO, P—Sn—O—F-based, PbO—$V_2O_5$—$TeO_2$, $Al_2O_3$—$H_2O$, and lead borosilicate.

The amount of the inorganic flame retardant blended is appropriately selected on the basis of the type of the inorganic flame retardant, other components of the curable resin composition, and the desired degree of flame retardancy. For example, preferably 0.05 to 20 parts by mass and particularly preferably 0.5 to 15 parts by mass of the inorganic flame retardant is contained in 100 parts by mass of a curable resin composition containing an epoxy resin, a curing agent, the non-halogen flame retardant, and other fillers and additives.

Examples of the organic metal salt-based blame retardant include ferrocene, acetylacetonate metal complex, organic metal carbonyl compounds, organic cobalt salt compounds, organic sulfonic acid metal salts, and a compound containing a metal atom ion-bonded or coordinate-bonded with an aromatic compound or a heterocyclic compound.

The amount of the organic metal salt-based flame retardant blended is appropriately selected on the basis of the type of the organic metal salt-based flame retardant, other components of the curable resin composition, and the desired degree of flame retardancy. For example, preferably 0.005 to 10 parts by mass of the organic metal salt-based flame retardant is contained in 100 parts by mass of a curable resin composition containing an epoxy resin, a curing agent, a non-halogen flame retardant, and other fillers and additives.

The curable resin composition may contain an inorganic filler if needed. Examples of the inorganic filler include fused silica, crystalline silica, alumina, silicon nitride and aluminum hydroxide. When the amount of the inorganic filler is to be particularly large, fused silica is preferably used. The fused silica may be in a crushed form or a spherical form; however, in order to increase the amount of the fused silica blended and suppress an increase in melt viscosity of a molding material, spherical fused silica is preferably mainly used. In order to increase the amount of spherical silica blended, the particle size distribution of the spherical silica is preferably appropriately adjusted. The fill ratio is preferably high considering the flame retardancy and is particularly preferably 20 mass % or more of the entire amount of the curable resin composition. When the curable resin composition is used in conductive paste or like usages, a conductive filler such as silver powder or copper powder can be used.

If needed, various additives such as a silane coupling agent, a releasing agent, a pigment, and an emulsifier may be added to the curable resin composition of the present invention.

The curable resin composition of the present invention can be obtained by homogeneously mixing the components described above. The curable resin composition can be easily formed into a cured product through processes the same as known processes. Examples of the cured product include shaped cured products such as a laminated product, a molded product, an adhesive layer, a coating film, and a film Examples of the usage for the curable resin composition according to the present invention include printed circuit board materials, resin compositions for flexible circuit boards, interlayer insulation materials for build-up substrates, semiconductor encapsulating materials, conductive paste, adhesive films for forming build-up structures, resin casting materials, and adhesives.

Regarding the use in printed circuit boards, insulating materials for electronic circuit boards, and adhesive films for forming build-up structures among these various usages, the curable resin composition can be used as an insulating material for electronics-embedded substrates in which passive parts such as capacitors and active parts such as IC chips are embedded in the substrates.

The curable resin composition is preferably used in printed circuit board materials, resin compositions for flexible circuit boards, and interlayer insulation materials for build-up substrates and is particularly preferably used in printed circuit boards due to properties such as high flame retardancy, high heat resistance, and solvent solubility.

An example of the method for manufacturing a printed circuit board of the present invention from the curable resin composition of the present invention is a method including impregnating a reinforcing substrate with a varnish-type curable resin composition containing an epoxy resin, a phosphorus-atom-containing oligomer composition, and an organic solvent, placing a copper foil thereon, and conducting heat-press bonding. Examples of the reinforcing substrate that can be used in this method include paper, glass cloth, glass non-woven cloth, aramid paper, aramid cloth, glass mat, and glass roving cloth. To be more specific, first, the varnish-type curable resin composition is heated to a heating temperature suitable for the type of solvent used and preferably to a temperature of 50 to 170° C. to obtain a pre-preg. The mass ratios of the resin composition and the reinforcing substrates used here may be any but are preferably adjusted so that the resin content in the pre-preg is 20 to 60 mass %. The pre-pregs obtained as such are stacked through a common method, copper foils are stacked as needed, and heat-bonding is performed at a pressure of 1 to 10 MPa at 170 to 250° C. for 10 minutes to 3 hours. As a result, a desired printed circuit board can be obtained.

In order to manufacture a flexible circuit board from the curable resin composition of the present invention, the phosphorus-atom-containing oligomer composition, an epoxy resin, an organic solvent, and, if needed, other curing agents and curing accelerators are mixed and applied to an electrically insulating film by using a coater such as a reverse roll coater, a comma coater, or the like. Then the applied mixture is dried with a heater at 60 to 170° C. for 1 to 15 minutes to evaporate the solvent and to cause the adhesive composition to enter the B-stage. Subsequently, a metal foil is heat-bonded to the adhesive by using a heating roller or the like. The press bonding pressure used at this time is preferably 2 to 200 N/cm and the heat bonding temperature is preferably 40 to 200° C. If sufficient adhesive performance is obtained by this process, the process may be ended here. However, if complete curing is necessary, post-curing is preferably further conducted at 100 to 200° C. for 1 to 24 hours. The thickness of the adhesive composition film after final curing is preferably within the range of 5 to 100 μm.

An example of the method for obtaining an interlayer insulation material for build-up substrates from the curable resin composition of the present invention is as follows. The curable resin composition containing rubber, a filler, etc., as necessary is applied by a spray coating method, a curtain coating method, or the like to a circuit board in which a circuit is formed, followed by curing. Then holes such as through holes are formed as needed, a treatment with a roughening agent is conducted, the surface is washed with hot water to form irregularities, and a metal such as copper is plated thereon. The plating method is preferably electroless plating or electroplating. Examples of the roughening agent include an oxidant, an alkali, and an organic solvent. This operation is sequentially repeated as needed to alternately build-up resin insulating layers and conductor layers having particular circuit patterns so as to obtain a build-up substrate. Through holes are formed after forming the outermost resin insulating layer. It is also possible to form a build-up substrate by heat-bonding at 170 to 250° C. a resin-clad copper foil prepared by semi-curing the resin composition on the copper foil onto a circuit board in which a circuit is formed so as to form a roughened surface and omit the step of plating.

An example of the method for manufacturing an adhesive film for forming build-up structures from the curable resin composition of the present invention is a method with which a resin composition film is formed on a supporting film by applying the curable resin composition of the present invention to the supporting film so as to form an adhesive film for multilayer printed circuit boards.

In using the curable resin composition of the present invention in an adhesive film for forming build-up structures, it is essential that the adhesive film soften at a laminating temperature condition (usually at 70° C. to 140° C.) of a vacuum lamination method and exhibit fluidity (resin flow) that allows via holes or through holes in the circuit board to be impregnated with the resin at the same time with lamination of the circuit board. Thus, the components described above are preferably blended so that these properties are exhibited.

Through holes in multilayer printed circuit boards usually have a diameter of 0.1 to 0.5 mm and a depth of 0.1 to 1.2 mm. It is usually preferable to enable resin impregnation within such ranges. When both sides of a circuit board are to be laminated, about ½ of through holes is preferably filled with resin.

The adhesive film can be manufactured by preparing a varnish-type curable resin composition of the present invention, applying the varnish-type composition to a surface of a supporting film, and drying the organic solvent by heating or blowing hot air so as to form a layer (α) of the curable resin composition.

The thickness of the layer (α) formed is usually equal to or greater than the thickness of a conductor layer. Since conductor layers of circuit boards typically have a thickness in the range of 5 to 70 μm, the resin composition layer preferably has a thickness of 10 to 100 μm.

The layer (α) may be protected with a protective film described below. When the layer is protected with a protective film, deposition of foreign matter on the resin composition layer surface and scratches can be prevented.

The supporting film and the protective film may be formed of a polyolefin such as polyethylene, polypropylene, or polyvinyl chloride, a polyester such as polyethylene terephthalate (hereinafter may be referred to as "PET") or polyethylene naphthalate, a polycarbonate, a polyimide, releasing paper, or a metal foil such as a copper foil or an aluminum foil. The supporting film and the protective film may be subjected to a MAD treatment, a corona treatment, or a releasing treatment.

The thickness of the supporting film may be any but is typically 10 to 150 μm and preferably in the range of 25 to 50 μm. The thickness of the protective film is preferably in the range of 1 to 40 μm.

The supporting film is removed after being laminated onto a circuit board or after formation of an insulating film by thermal curing. Deposition of foreign matter and the like during the curing step can be prevented by removing the supporting film after thermally curing the adhesive film. In the case where the supporting film is to be removed after curing, the supporting film is subjected to a releasing treatment in advance.

The method for manufacturing a multilayer printed circuit board by using the adhesive film obtained as above includes, for example, removing a protective film if the layer (α) is protected with the protective film, and laminating the layer (α) onto one or both sides of the circuit board by a vacuum lamination technique, for example, so that the layer (α) directly contacts the circuit board. The lamination method may be batch or continuous using rolls. If needed, the adhesive film and the circuit board may be heated (pre-heated) prior to conducting lamination.

Lamination is preferably conducted at a press-bonding temperature (laminating temperature) of 70 to 140° C. at a press-bonding pressure of 1 to 11 kgf/cm$^2$ ($9.8 \times 10^4$ to $107.9 \times 10^4$ N/m$^2$) and at a reduced pressure, i.e., an air pressure of 20 mmHg (26.7 hPa) or less.

In the case where the curable resin composition of the present invention is used in conductive paste, a method with which a composition for forming an anisotropic conductive film is formed by dispersing conductive fine particles in the curable resin composition or a method with which the curable resin composition is prepared into a paste resin composition for circuit interconnection, the paste being liquid at room temperature, or an anisotropic adhesive may be employed, for example.

A semiconductor encapsulating material can be obtained from the curable resin composition of the present invention by, for example, mixing the phosphorus-atom-containing oligomer composition, the epoxy resin, a curing accelerator, and additives such as an inorganic filler and thoroughly melt-mixing the resulting mixture by using an extruder, a kneader, a roller, or the like as needed until the mixture is homogeneous. During this process, silica is typically used as the inorganic filler and the filler ratio is preferably in the range of 30 to 95 mass % per 100 parts by mass of the curable resin composition. In particular, the filler ratio is preferably 70 parts by mass or more to improve the flame retardancy, moisture resistance, and solder cracking resistance and decrease the linear expansion coefficient and the filler ratio is more preferably 80 parts by mass or more in order to further enhance these effects. An example of semiconductor package molding is a method that includes molding the composition by using a mold, a transfer molding machine, an injection molding machine, or the like and heating the molded composition at 50 to 200° C. for 2 to 10 hours so as to obtain a molded product, which is a semiconductor device.

The method for obtaining a cured product according to the present invention may be a performed through a typical method for curing a curable resin composition. For example, the heating temperature condition may be appropriately selected on the basis of the curing agent used in combination and usage. For example, the composition obtained by the above-described method may be heated at a temperature in the range of about 20 to 250° C.

EXAMPLES

The present invention will now be described specifically by using Examples and Comparative Examples. The melt viscosity at 180° C., the softening point, the phosphorus content, the GPC, NMR, and the MS spectrum were measured under the following conditions:
1) Melt viscosity at 180° C.: Measured in accordance with ASTM D4287
2) Softening point measurement method: JIS K7234
3) Phosphorus content measurement method: Measured in accordance with JIS K0102-46
4) GPC: Measurement conditions were as follows:
Measurement instrument: "HLC-8220 GPC" produced by Tosoh Corporation
Column: Guardcolumn "HXL-L" produced by Tosoh Corporation
  "TSK-GEL G2000HXL" produced by Tosoh Corporation
  "TSK-GEL G2000HXL" produced by Tosoh Corporation
  "TSK-GEL G3000HXL" produced by Tosoh Corporation
  "TSK-GEL G4000HXL" produced by Tosoh Corporation
Detector: RI (differential refractometer)
Data processing: "GPC-8020 Model II, version 4.10" produced by Tosoh Corporation
Measurement Conditions
  Column temperature: 40° C.
  Developing solvent: tetrahydrofuran
  Flow rate: 1.0 ml/min
Standard: In accordance with a measurement manual of "GPC-8020 Model II, version 4.10" described above, monodisperse polystyrenes below whose molecular weights are known were used:
(Polystyrenes Used)
  "A-500" produced by Tosoh Corporation
  "A-1000" produced by Tosoh Corporation
  "A-2500" produced by Tosoh Corporation
  "A-5000" produced by Tosoh Corporation
  "F-1" produced by Tosoh Corporation
  "F-2" produced by Tosoh Corporation
  "F-4" produced by Tosoh Corporation
  "F-10" produced by Tosoh Corporation
  "F-20" produced by Tosoh Corporation
  "F-40" produced by Tosoh Corporation
  "F-80" produced by Tosoh Corporation
  "F-128" produced by Tosoh Corporation
Sample: Sample prepared by filtering a tetrahydrofuran solution having a resin solid content of 1.0 mass % with a microfilter (50 μl).
5) NMR: JNM-ECA500 model nuclear magnetic resonance spectrometer produced by JEOL Ltd.
  Magnetic field strength: 500 MHz
  Pulse width: 3.25 μsec
  Number of runs: 8000
  Solvent: DMSO-d6
  Sample density: 30 mass %
6) MS: "AXIMA-TOF2" produced by Shimadzu Biotech
  Measurement mode: linear
  Number of runs: 100
  Composition of sample: sample/DHBA/NaTFA/THF=10.0 mg/100.0 mg/5.0 mg/1 ml The ratio of the component having 1 or more repeating units represented by structural formula 1 above (hereinafter simply referred to as "n=1 or more") was calculated on the basis of the peak area less than 36.0 minutes in a GPC chart.

Example 1

Into a flask equipped with a thermometer, a cooling tube, a fractionating column, and a stirrer, 324.0 parts by mass (1.5 mol) of 9,10-dihydro-9-oxa-10-phosphaphenanthrene-10-oxide and 122 parts by mass (1.0 mol) of o-hydroxybenzaldehyde were charged, and stirring was conducted at 40° C. while blowing nitrogen. The mixture was heated to 140° C., stirred for 4 hours, heated to 180° C., and stirred for 8 hours. Then water was removed by heating under a reduced pressure. As a result, 410 parts by mass of a phosphorus-atom-containing oligomer composition (A-1) represented by formula below was obtained:

[Chem. 9]

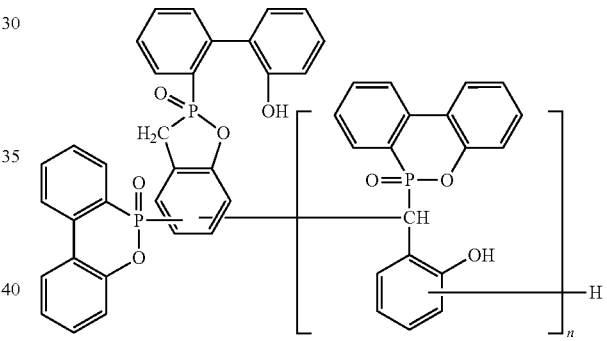

Figure 2:
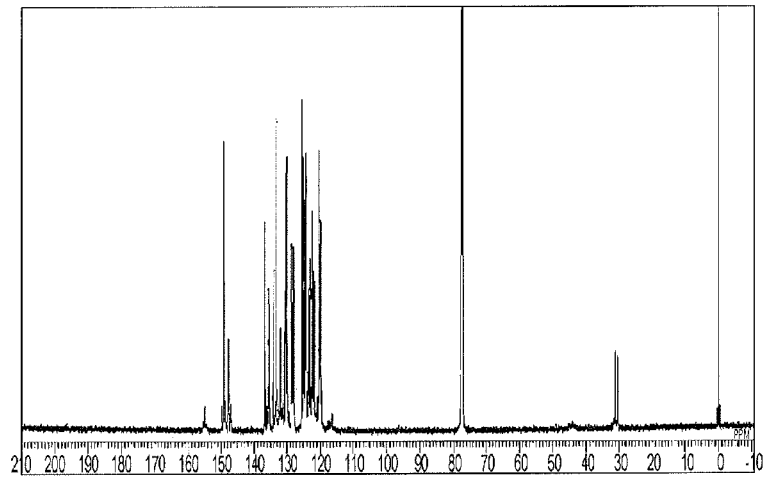
FIG. 2 is a $^{13}$C-NMR chart of the phosphorus-atom-containing oligomer composition (A-1) obtained in Example 1.
Figure 3:
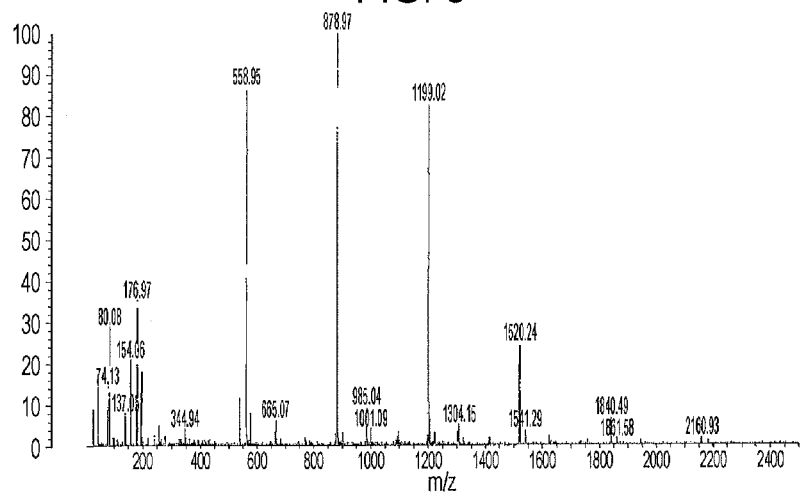
FIG. 3 is a MS spectrum of the phosphorus-atom-containing oligomer composition (A-1) obtained in Example 1.

The hydroxyl equivalent of the phosphorus-atom-containing oligomer composition obtained was 428 g/equivalent, the softening point was 140° C., and the phosphorus content was 10.5%. The ratio of the phosphorus-atom-containing compound with n representing 0 was 53.3% and the ratio of the compound with n representing 1 or more was 46.7%. A GPC chart of the phosphorus-atom-containing oligomer (A-1) is shown in FIG. 1, a $^{13}$C-NMR chart in FIG. 2, and a MS spectrum in FIG. 3.

Example 2

Into a flask equipped with a thermometer, a cooling tube, a fractionating column, and a stirrer, 324.0 parts by mass (1.5 mol) of 9,10-dihydro-9-oxa-10-phosphaphenanthrene-10-oxide and 122 parts by mass (1.0 mol) of o-hydroxybenzaldehyde were charged, and stirring was conducted at 40° C. while blowing nitrogen. The mixture was heated to 140° C., stirred for 1 hour, heated to 180° C., and stirred for 8 hours. Then water was removed by heating under a reduced pressure. As a result, 415 parts by weight of a phosphorus-atom-containing oligomer composition (A-2) represented by formula below was obtained:

[Chem. 10]

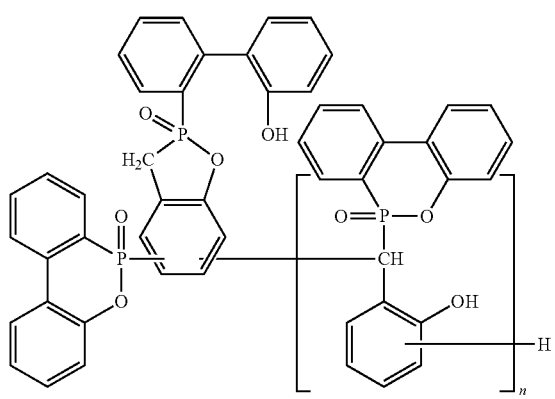

Figure 4:
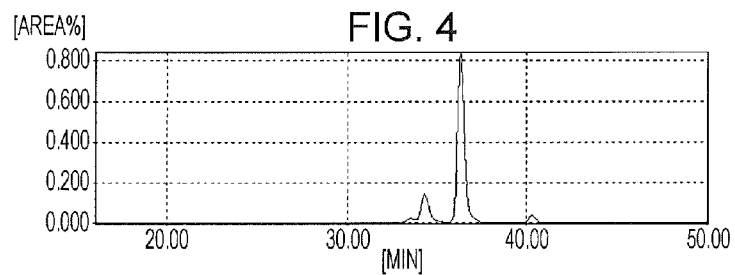
FIG. 4 is a GPC chart of a phosphorus-atom-containing oligomer composition (A-2) obtained in Example 2.

The hydroxyl equivalent of the phosphorus-atom-containing oligomer composition obtained was 428 g/equivalent, the softening point was 120° C., and the phosphorus content was 10.5%. The ratio of the phosphorus-atom-containing compound with n representing 0 was 80.6% and the ratio of the compound with n representing 1 or more was 19.4. A GPC chart of the phosphorus-atom-containing oligomer (A-2) is shown in FIG. 4.

Example 3

Into a flask equipped with a thermometer, a cooling tube, a fractionating column, and a stirrer, 324.0 parts by mass (1.5 mol) of 9,10-dihydro-9-oxa-10-phosphaphenanthrene-10-oxide and 122 parts by mass (1.0 mol) of o-hydroxybenzaldehyde were charged, and stirring was conducted at 40° C. while blowing nitrogen. The mixture was heated to 140° C., stirred for 8 hours, heated to 180° C., and stirred for 8 hours. Then water was removed by heating under a reduced pressure. As a result, 400 parts by mass of a phosphorus-atom-containing oligomer composition (A-3) represented by formula below was obtained:

[Chem. 11]

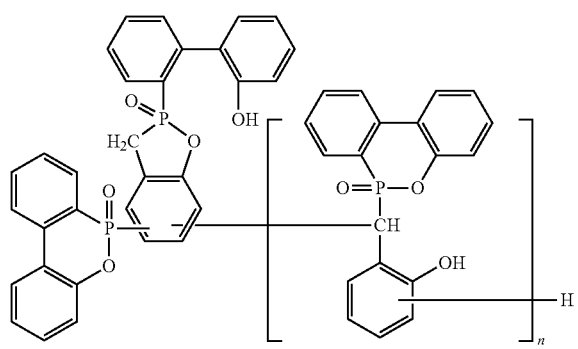

Figure 5:
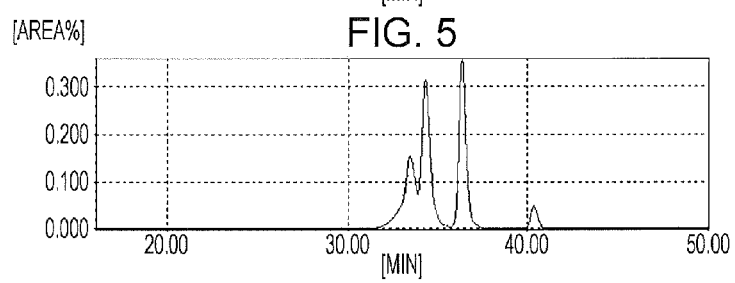
FIG. 5 is a GPC chart of a phosphorus-atom-containing oligomer composition (A-3) obtained in Example 3.

The hydroxyl equivalent of the phosphorus-atom-containing oligomer composition obtained was 428 g/equivalent, the softening point was 148° C., and the phosphorus content was 10.5%. The ratio of the phosphorus-atom-containing compound with n representing 0 was 38.6% and the ratio of the compound with n representing 1 or more was 61.4%. A GPC chart of the phosphorus-atom-containing oligomer (A-3) is shown in FIG. 5.

Comparative Example 1

Synthesis of a Compound Described in PTL 2

Into a flask equipped with a thermometer, a cooling tube, a fractionating column, a nitrogen gas inlet tube, and a stirrer, 122 g (1.0 mol) of p-hydroxybenzaldehyde, 216 g (1.0 mol) of 9,10-dihydro-9-oxa-10-phosphaphenanthrene-10-oxide (hereinafter simply referred to as "HCA"), and 336 g of 2-propanol were charged, and refluxing was conducted for 5 hours. White solid precipitates were filtered out, washed with 1000 mL of 2-propanol, and dried. As a result, 325 g (yield: 96%) of a phenol compound (A-4) having a structure represented by the formula below was obtained:

[Chem. 12]

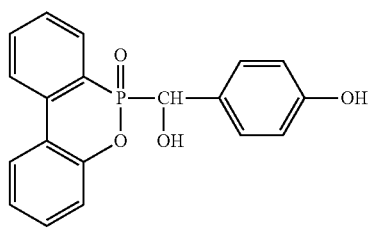

Figure 6:
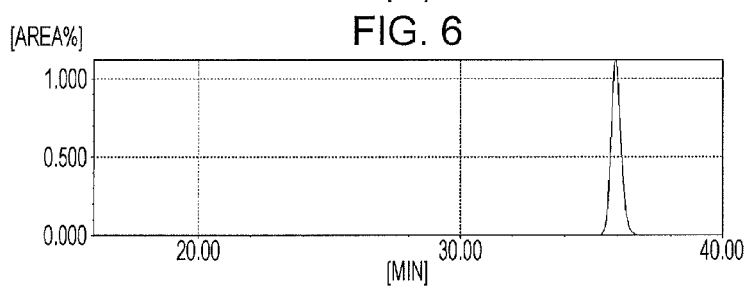
FIG. 6 is a GPC chart of a phenol compound (A-4) obtained in Comparative Example 1.

A GPC chart of the obtained phenol compound (A-4) is shown in FIG. 6.

Comparative Example 2

Compound Described in NPL 1

Into a flask equipped with a thermometer, a cooling tube, a fractionating column, a nitrogen gas inlet tube, and a stirrer, 236.6 g (0.7 mol) of the phenol compound (A-4) obtained in Comparative Example 1 and 3.08 g (0.034 mol) of oxalic acid were charged, and the mixture was stirred under heating at 180° C. for 3 hours. Subsequently, water was removed by heating under a reduced pressure. As a result, 210 g of a phenol resin (A-5) having, as a main component, a structural unit represented by the formula below was obtained:

[Chem. 13]

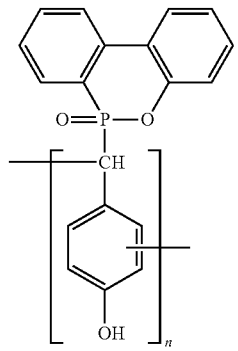

Figure 7:
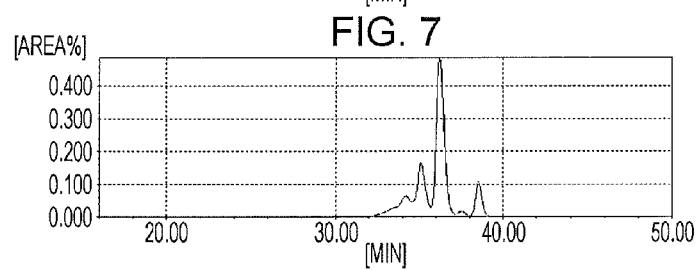
FIG. 7 is a GPC chart of a phenol compound (A-5) obtained in Comparative Example 2.

The softening point was 84° C. (B&R method), the melt viscosity (measurement method: ICI viscometer method, measurement temperature: 150° C.) was 1.0 dPa·s, the hydroxyl equivalent was 420 g/equivalent, the phosphorus content was 9.4 mass %, and the ratio of the component with n representing 2 or more was 34.0% A GPC chart of the obtained phenolic resin (A-5) is shown in FIG. 7.

Comparative Example 3

Compound Described in PTL 1

Into a flask equipped with a thermometer, a cooling tube, a fractionating tube, a nitrogen gas inlet tube, and a stirrer, 169 g (0.5 mol) of the phenol compound (A-4) obtained in Comparative Example 1, 47 g (0.5 mol) of phenol, and 1.25 g of p-toluenesulfonic acid were charged. The mixture was heated to 180° C., reacted at 180° C. for 8 hours, filtered, and dried. As a result, 199 g of a phenol compound (A-6) represented by structural formula below was obtained:

[Chem. 14]

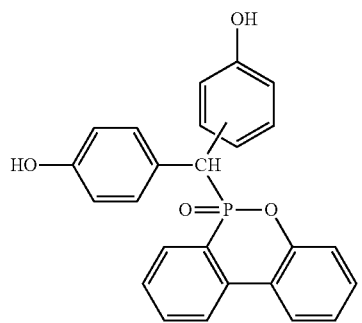

Figure 8:
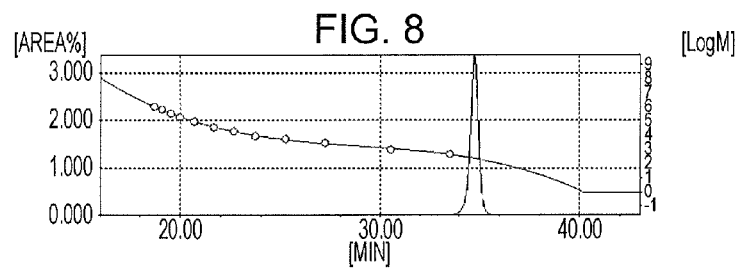
FIG. 8 is a GPC chart of a phenol compound (A-6) obtained in Comparative Example 3.

The melting point of the phenol compound (A-6) was 286° C. A GPC chart of the phenol compound (A-6) obtained is shown in FIG. 8.

Examples 4 to 6 and Comparative Examples 4 to 6

Preparation of Epoxy Resin Compositions and Evaluation of Physical Properties

In accordance with the blend formulations described in Table 1, epoxy resins, i.e., "N-690" produced by DIC Corporation (phenol novolac-type epoxy resin, epoxy equivalent: 215 g/eq) and "FX-289BEK75" produced by Nippon Steel Chemical Co., Ltd. (phosphorus-containing modified epoxy resin, epoxy equivalent: 330 g/eq), and curing agents, i.e., phosphorus-containing phenolic resins (A-1), (A-2), (A-3), (A-5), (A-6) and a phenol novolac resin ("TD-2090" produced by DIC corporation, hydroxyl equivalent: 105 g/eq) were blended, 2-ethyl-4-methylimidazole (2E4MZ) was added as a curing catalyst, and methyl ethyl ketone was added so that the nonvolatile content (NV) of each composition was ultimately 58 mass %.

[Laminated Board Manufacturing Conditions]

Substrate: 100 μm, "2116" glass cloth for printed circuit boards produced by Nitto Boseki Co., Ltd., number of plies: 6

Copper foil: 18 μm, TCR foil produced by Nippon Mining & Metals Co., Ltd.

Conditions for pre-impregnation: 160° C./2 minutes

Curing conditions: 200° C., 2.9 MPa, 2.0 hours

Thickness after forming: 0.8 mm, resin content: 40%

A cured product prepared under the above-described conditions was used as a test piece and various types of evaluation was conducted. The results are shown in Table 1.

[Physical Property Testing Conditions]

Glass transition point: After removing the copper foil by etching, the test piece was measured by a TMA method (compressive load method). The heating rate was 3° C./min.

Heat peeling resistance test (time to delamination): Heat peeling resistance at 288° C. was evaluated (copper clad) in accordance with IPC TM650.

Combustion test: Test was performed in accordance with UL-94 vertical test.

Heat peeling resistance test (T288 test): Heat peeling resistance was evaluated (copper clad) at 288° C. in accordance with IPC TM650.

TABLE 1

| | | Example | | | Comparative Example | | |
|---|---|---|---|---|---|---|---|
| | | 4 | 5 | 6 | 4 | 5 | 6 |
| Epoxy resin | N-690 | 57 | 57 | 57 | 34 | 40 | |
| | FX-289BEK75 | | | | | | 76 |
| Curing agent | A-1 | 19 | | | | | |
| | A-2 | | 19 | | | | |
| | A-3 | | | 19 | | | |
| | A-5 | | | | 66 | | |
| | A-6 | | | | | 60 | |
| | TD-2090 | 23 | 23 | 23 | | | 24 |
| Curing accelerator | 2E4MZ (mass %) | 0.1 | 0.1 | 0.1 | 0.1 | 0.1 | 0.1 |
| P content in curable composition (mass %) | | 2 | 2 | 2 | 4.8 | 5.6 | 2.3 |
| Heat resistance | Glass transition point (° C.) | 153 | 149 | 158 | Evaluation was not possible due to precipitation of crystals | Evaluation was not possible due to precipitation of crystals | 129 |
| Thermal decomposition resistance | T288 (min) | >120 | >120 | >120 | | | 0 |

TABLE 1-continued

|  |  | Example | | | | | |
|---|---|---|---|---|---|---|---|
|  |  | 4 | 5 | 6 | 4 | 5 | 6 |
| Flame retardancy | Total combustion time (sec) | 26 | 29 | 24 |  |  | 45 |
|  | Evaluation | V-0 | V-0 | V-0 |  |  | V-0 |

Legend in Table 1:
N-690: Cresol novolac-type epoxy resin produced by DIC Corporation ("EPICLON N-690", epoxy equivalent: 215 g/eq)
FX-289BEK75: Phosphorus-modified epoxy resin ("FX-289BER75") produced by Tohto Kasei Co., Ltd., epoxy resin obtained by allowing a cresol novolac-type epoxy resin to react with 9,10-dihydro-9-oxa-10-phosphaphenanthrene-10-oxide, epoxy equivalent: 330 g/eq, P content: 3.0 mass %)
A-1: Phosphorus-atom-containing oligomer composition (A-1) obtained in Example 1.
A-2: Phosphorus-atom-containing oligomer composition (A-2) obtained in Example 2.
A-3: Phosphorus-atom-containing oligomer composition (A-3) obtained in Example 3.
A-5: Phosphorus-atom-containing oligomer composition (A-5) obtained in Comparative Example 2.
A-6: Phosphorus-atom-containing oligomer composition (A-6) obtained in Comparative Example 3.
TD-2090: Phenol novolac-type phenolic resin ("TD-2090" produced by DIC Corporation, hydroxyl equivalent: 105 g/eq)
2E4MZ: 2-Ethyl-4-methylimidazole

The invention claimed is:

1. A phosphorus-atom-containing oligomer composition comprising a mixture of a phosphorus-atom-containing compound represented by structural formula (1) below with n representing 0 and a phosphorus-atom-containing oligomer represented by structural formula (1) below with n representing 1 or more:

[Chem. 1]

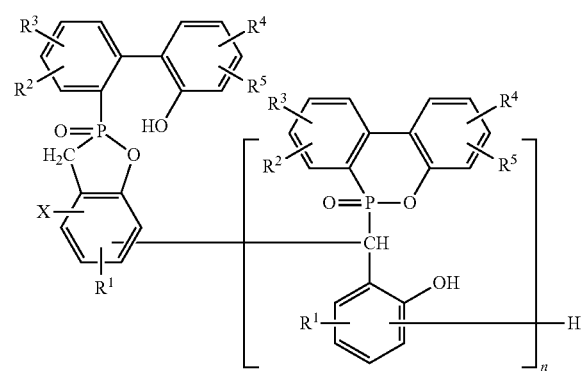

(1)

(where $R^1$ to $R^5$ each independently represent a hydrogen atom, an alkyl group having 1 to 4 carbon atoms, an alkoxy group having 1 to 4 carbon atoms, or a phenyl group; X represents a hydrogen atom or a structural unit represented by structural formula (x1) below:

[Chem. 2]

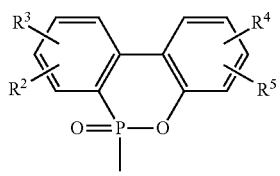

(x1)

where, in structural formula (x1), $R^2$ to $R^5$ each independently represent a hydrogen atom, an alkyl group having 1 to 4 carbon atoms, an alkoxy group having 1 to 4 carbon atoms, or a phenyl group; and n represents the number of repeating units and is an integer of 0 or more), wherein a content of the phosphorus-atom-containing oligomer represented by general structural formula (1) with n representing 1 or more is in the range of 5 to 90% on a peak area basis in GPC measurement.

2. The phosphorus-atom-containing oligomer composition according to claim 1, wherein a phosphorus atom content is 9 to 12 mass %.

3. A curable resin composition comprising an epoxy resin and a curing agent as essential components, wherein the phosphorus-atom-containing oligomer composition according to claim 1 is used as the curing agent.

4. A cured product obtained by curing the curable resin composition according to claim 3.

5. A printed circuit board obtained by blending an organic solvent with the curable resin composition according to claim 3 to prepare a varnish-type resin composition, impregnating a reinforcing substrate with the varnish-type resin composition, placing a copper foil thereon, and conducting thermal press bonding.

6. A curable resin composition comprising an epoxy resin and a curing agent as essential components, wherein the phosphorus-atom-containing oligomer composition according to claim 2 is used as the curing agent.

* * * * *